(12) United States Patent
Di Sessa et al.

(10) Patent No.: US 8,540,700 B2
(45) Date of Patent: *Sep. 24, 2013

(54) DISPOSABLE TIP ASSEMBLY FOR LASER SURGICAL DEVICE

(71) Applicant: Zila, Inc., Fort Collins, CO (US)

(72) Inventors: Alexandre B. Di Sessa, Walnut Creek, CA (US); Mihai I. A. Boitor, Pleasant Hill, CA (US)

(73) Assignee: Zila, Inc., Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/622,618

(22) Filed: Sep. 19, 2012

(65) Prior Publication Data

US 2013/0018365 A1    Jan. 17, 2013

Related U.S. Application Data

(63) Continuation of application No. 12/115,336, filed on May 5, 2008, now Pat. No. 8,277,442.

(51) Int. Cl.
*A61B 18/18* (2006.01)

(52) U.S. Cl.
USPC .................................. 606/1; 606/15; 606/16

(58) Field of Classification Search
USPC ..................................................... 606/1–19
See application file for complete search history.

(56) References Cited

U.S. PATENT DOCUMENTS

| | | | |
|---|---|---|---|
| 4,526,170 A | 7/1985 | Tanner | |
| 4,785,805 A | 11/1988 | Joffe | |
| 4,895,145 A | 1/1990 | Joffe | |
| 5,304,172 A | 4/1994 | Manoukian | |
| 5,364,391 A | 11/1994 | Konwitz | |
| 5,464,436 A | 11/1995 | Smith | |
| 5,607,420 A | 3/1997 | Schuman | |
| 5,616,141 A | 4/1997 | Cipolla | |
| 5,927,977 A | 7/1999 | Sale | |
| 5,928,220 A | 7/1999 | Shimoji | |
| 5,951,544 A | 9/1999 | Konwitz | |
| 6,013,096 A | 1/2000 | Tucek | |
| 6,039,565 A | 3/2000 | Chou | |
| 6,059,776 A | 5/2000 | Gatto | |
| 6,099,520 A | 8/2000 | Shimoji | |
| 6,213,998 B1 | 4/2001 | Shen | |
| 6,231,567 B1 | 5/2001 | Rizoiu | |
| 6,254,597 B1 | 7/2001 | Rizoiu | |
| 6,261,310 B1 | 7/2001 | Neuberger | |
| 6,325,791 B1 | 12/2001 | Shimoji | |
| 6,327,942 B1 | 12/2001 | Mariol | |
| 6,458,120 B1 | 10/2002 | Shen | |
| 6,572,637 B1 | 6/2003 | Yamazaki | |
| 6,574,401 B2 | 6/2003 | Neuberger | |
| 6,746,473 B2 | 6/2004 | Shanks | |
| D496,101 S | 9/2004 | Davison | |

(Continued)

FOREIGN PATENT DOCUMENTS

WO    01/10327 A1    2/2001

*Primary Examiner* — Sam Yao
*Assistant Examiner* — Nathan J Jenness
(74) *Attorney, Agent, or Firm* — Jeffer Mangels Butler & Mitchell LLP

(57) ABSTRACT

A multi-component sterile, disposable tip apparatus for laser surgical devices is provided and features assembly for alignment of a self-contained optical fiber to the surgical device and releasably locking assembly between the tip and device.

12 Claims, 4 Drawing Sheets

(56) References Cited

U.S. PATENT DOCUMENTS

| | | |
|---|---|---|
| 6,868,221 B1 | 3/2005 | Wood |
| 7,033,350 B2 | 4/2006 | Bahk |
| 7,118,563 B2 | 10/2006 | Weckwerth |
| 7,137,977 B2 | 11/2006 | Brucker |
| 7,267,672 B2 | 9/2007 | Allshuler |
| 7,288,086 B1 | 10/2007 | Andriasyan |
| 7,290,940 B2 | 11/2007 | Boutoussov |
| 7,320,594 B1 | 1/2008 | Rizoiu |
| 7,695,469 B2 | 4/2010 | Boutoussov |
| 2002/0081080 A1 | 6/2002 | Balle-Petersen |
| 2004/0259053 A1 | 12/2004 | Bekov |
| 2006/0064080 A1 | 3/2006 | Cao |
| 2008/0154249 A1 | 6/2008 | Cao |
| 2008/0161783 A1 | 7/2008 | Cao |
| 2008/0181261 A1* | 7/2008 | Boutoussov et al. ............. 372/6 |
| 2010/0069899 A1* | 3/2010 | Lonero et al. .................. 606/15 |

* cited by examiner

DISPOSABLE TIP ASSEMBLY FOR LASER SURGICAL DEVICE

CROSS-REFERENCES TO RELATED APPLICATIONS

This application is a continuation of U.S. patent application Ser. No. 12/115,336, filed May 5, 2008, the entirety of which is incorporated herein by reference.

STATEMENT REGARDING FEDERALLY SPONSORED RESEARCH OR DEVELOPMENT

None.

REFERENCE TO A MICRO-FICHE APPENDIX

None.

BACKGROUND OF THE INVENTION

This invention relates to surgical instruments for laser ablation procedures. More particularly, the invention relates to a sterile, disposable tip apparatus for such surgical instruments.

BRIEF SUMMARY OF THE INVENTION

Medical laser treatment using hand-held instruments has generally been developed for ophthalmic, dental, orthopedic, and similar surgical procedures where the treatment area is confined or particularly difficult to reach. Typically, laser light is transmitted from a laser source though an optical fiber to a treatment site. The optical fiber terminates proximally in a laser source connector for connection to the laser source and terminates distally in a handpiece manipulated by the surgeon.

A handpiece used during one procedure cannot be used with another patient in a subsequent procedure unless some form of sterilization is performed. Types of sterilization techniques range from autoclaves to gas. Gas procedures are time consuming and costly. Autoclave temperatures generally have proven too severe for laser surgical handpieces to withstand.

Accordingly it would be useful to provide a sterile, disposable tip for use with a laser surgical device.

It would be of further use if the sterile, disposable tip provided means for precise alignment of the optical fiber in the tip to the source of laser energy in the surgical device.

Yet another useful advantage would be for the sterile, disposable tip to be releasably attached to the device with precise optical, mechanical, magnetic, electro-mechanical, or electro-magnetic locking and alignment assembly.

Other features, advantages, and objects of the present invention will become apparent with reference to the following description and accompanying drawings.

DETAILED DESCRIPTION OF THE INVENTION

Figure 1:
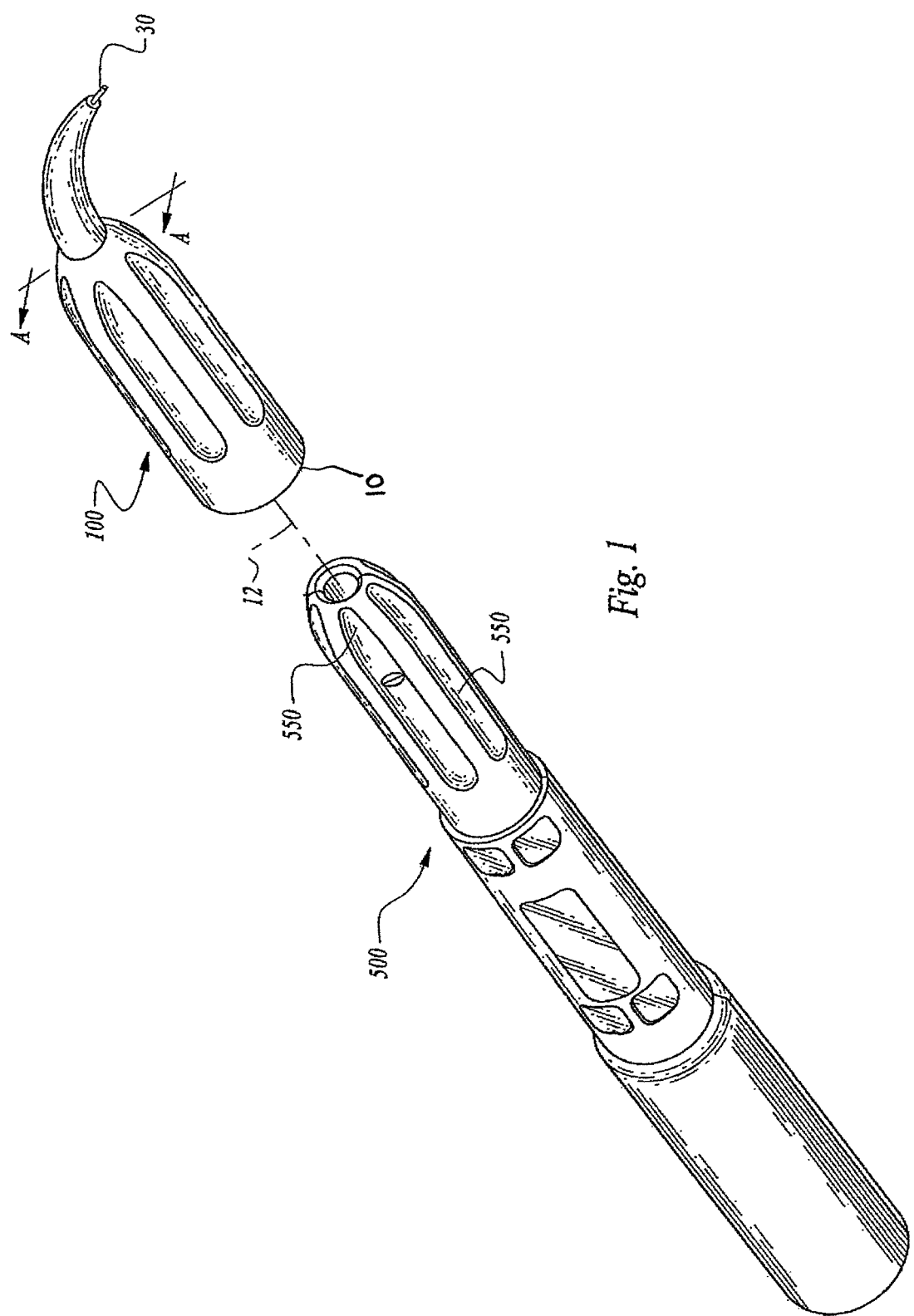
FIG. 1 is a perspective view of an embodiment of disposable tip apparatus 100 adapted to reusable laser surgical device 500.

With reference to drawing FIGS. 1-4, disposable tip apparatus 100 for reusable laser surgical device is presented.

The tip apparatus 100 comprises in combination: a first end 10 having a longitudinal axis 12 and adapted to releasably fit on the distal end of the surgical device 500; second end 20 tapering to a discharge tip 22; optical fiber means 30 for delivery of light energy axially positioned within the tip apparatus from within the first end 10 and extending beyond the discharge tip 22; means for removably locking the first end 10 to the surgical device 500 and connecting the first end 10, second end 20, and optical fiber means 30; and means for aligning fiber optic means 30 within the tip apparatus 10 with the surgical device 500 for surgical laser treatment.

An embodiment of the tip apparatus 100 provides means for aligning the optical fiber means within the tip apparatus with the surgical device comprising a sleeve on the tip first end.

Another embodiment of tip apparatus 100 provides means for aligning the optical fiber means within the tip apparatus with the surgical device comprises at least two slits 550 spaced equally apart on the distal end of the surgical device 500 and a tip first end sleeve 16 having internal longitudinal ribs 18 adapted to fit the surgical device slits 550. In this manner, the tip apparatus 100 is secured to the surgical device 500 in such a way as to allow freedom of movement in only one dimension, along the longitudinal axis 12.

An embodiment of the tip apparatus 100 provides a discharge tip end is along (not shown) the first end longitudinal axis 12.

Figure 2:
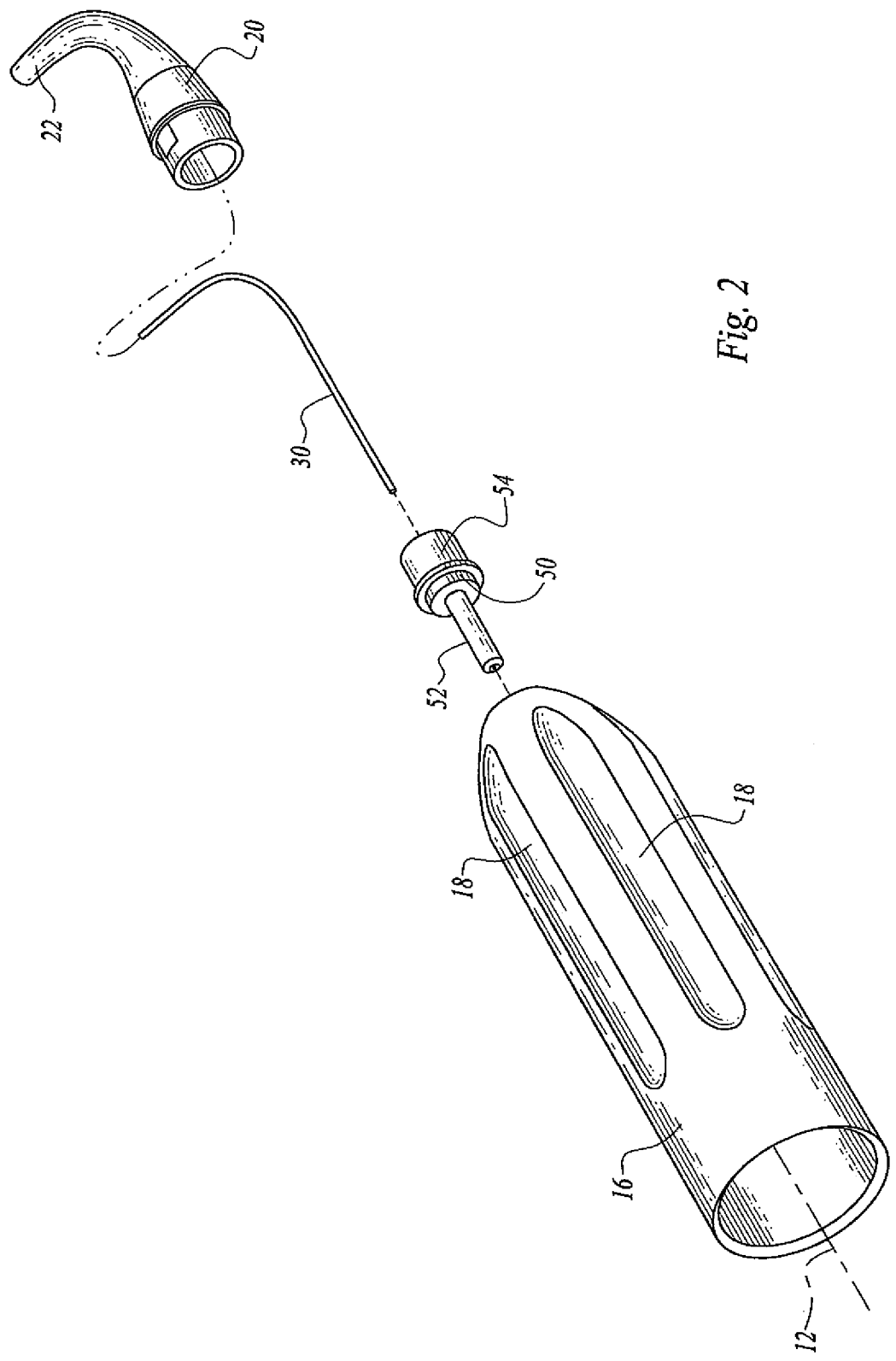
FIG. 2 is an exploded perspective view of the embodiment of disposable tip apparatus 100 of FIG. 1.
Figure 3:
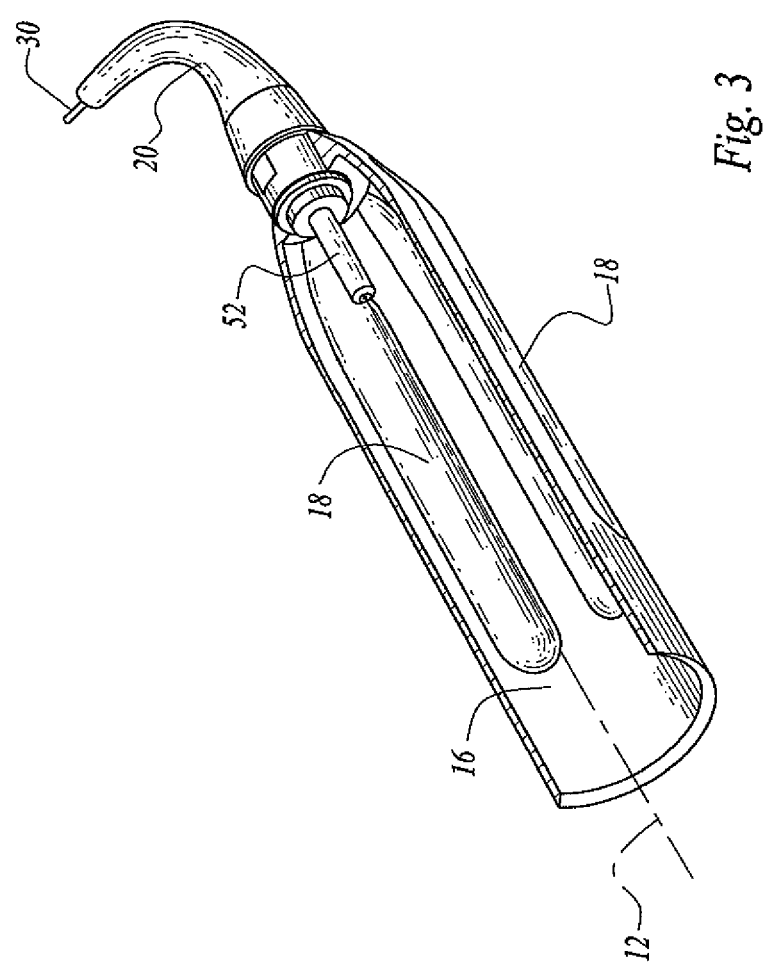
FIG. 3 is a cross sectional view of the embodiment of disposable tip apparatus 100 of FIG. 1 taken at "A-A."
Figure 4:
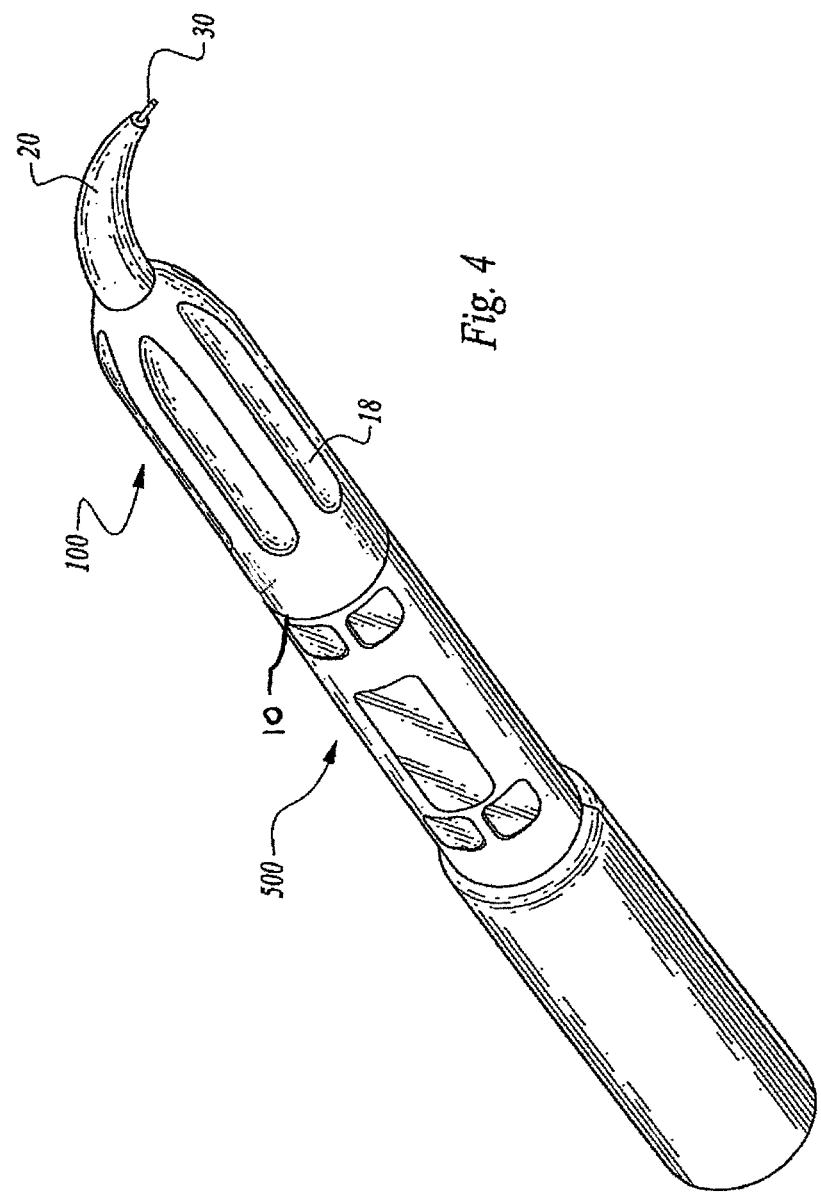
FIG. 4 is a perspective view of disposable tip apparatus 100 of FIG. 1 engaged with a reusable laser surgical device 500.

Another embodiment of tip apparatus 100 provides the discharge tip 22 end at an acute angle to the first end 10 longitudinal axis 12, FIGS. 1-3.

Yet another embodiment of tip apparatus 100 provides the discharge tip 22 end at a right angle (not shown) to the first end longitudinal axis 12.

As depicted in FIGS. 2 and 3, the first end 10, second end 20, and fiber optic means 30 communicate via a common connector 50 comprising a probe 52 and housing 54 adapted to the second end 20. The probe 52 and housing 54 further comprise an axial orifice size to receive and contain fiber optic means 30.

The probe 52 and housing 54 further comprise means for releasably locking the first end 10 to the surgical device 500 comprises at least one member of the group consisting of means for magnetic coupling, means for mechanical coupling, means for electro-mechanical coupling, and means for electro-magnetic coupling. The preferred embodiment of tip apparatus 100 comprises magnetic material in the housing 54 which, when the tip apparatus 100 is positioned on the surgical device 500, is proximate to a magnet within the surgical device 500, releasably locking the tip apparatus 100 to the surgical device 500.

The tip apparatus 100 first end 10 and second end 20 are made of at least one member of the group consisting of polyimide, polycarbon, stainless steel, and steel, iron, plastic aluminum, and the like materials.

In a preferred embodiment of disposable tip assembly 10 for reusable surgical laser treatment device 500, the tip assembly 10 is packaged as a sterile assembly and comprises in combination: a first sleeved end 16 adapted to releasably fit on the device 500 and having a longitudinal axis 12; a second cannula end 20 tapering to a discharge tip 22; optical fiber means 30 for delivery of light energy axially positioned within the tip assembly 10 and extending beyond the discharge tip 22; means for removably locking the first sleeved end 16 to the device 500, and connecting the first sleeved end 16, second cannula end 20, and optical fiber means 30; and means for aligning fiber optic means 30 within the tip assembly 10 with reusable device 500 for surgical laser treatment.

Means for aligning the optical fiber means 30 within the tip assembly 10 with the surgical device 500 comprises at least two slits 550 spaced equally apart on the distal end of the surgical device 500 and internal longitudinal ribs 18 on the sleeve 16 adapted to fit the surgical device slits 550. These slits 550 and corresponding ribs 18 are precisely machined to high tolerance in such a manner that the precision of alignment of optical fiber means 30 within the tip assembly 10 with the surgical device 500 is not dependent upon the strength or size of magnetic material in the housing 54 or the surgical device 500. This alignment assembly allows variable rotation of the tip assembly 10 with the surgical device 500 to allow use of the same surgical device 500 device by right- or left-handed surgeons.

For a preferred embodiment of sterile polyimide sleeve assembly 10 for reusable laser surgical device 500, the sleeve assembly comprises in combination: a first end 10 having a longitudinal axis 12 and adapted to releasably fit on a distal end of the surgical device 550; a cannula second end 20 tapering to a discharge tip 22 at an acute downward angle to the first end longitudinal axis 12; optical fiber means 30 for delivery of light energy axially positioned within the tip assembly from within the first end 10 and extending beyond the discharge tip 22; magnetic means 50 for releasably locking the first end to the surgical device distal end and connecting the first end 10, cannula second end 20, and optical fiber means 30; and six slits 550 spaced sixty degrees apart on the distal end of the surgical device 500 and first end internal longitudinal ribs 18 adapted to fit the surgical device slits 550.

We claim:

1. A disposable tip assembly for a laser surgical device, the tip assembly comprising:
   a hollow sleeve having a first opening for removably receiving a portion of the laser surgical device and a second opening defined in a distal end thereof, wherein the sleeve includes a plurality of spaced apart longitudinally extending internal ribs adapted to be received in corresponding slits on the laser surgical device,
   a tip member having a hollow interior and that is partially received in the second opening in the sleeve,
   a connector having an orifice extending axially therethrough, wherein at least a portion of the connector is received in the hollow interior of the tip member, and
   an optical fiber that extends through the axial orifice of the connector and the hollow interior of the disposable tip member.

2. The disposable tip assembly of claim 1 wherein the connector includes a housing and a probe, wherein the housing is received in the disposable tip member and the probe extends into the hollow sleeve.

3. The disposable tip assembly of claim 2 wherein the housing comprises a magnetic material.

4. The disposable tip assembly of claim 3 wherein the housing has a larger diameter than the probe.

5. The disposable tip assembly of claim 1 wherein the tip member tapers to a discharge tip end.

6. The disposable tip assembly of claim 5 wherein the sleeve defines a longitudinal axis, and wherein the discharge tip end is at a right angle to the sleeve longitudinal axis.

7. The disposable tip assembly of claim 1 wherein the connector comprises a magnetic material.

8. A disposable tip assembly for a reusable surgical laser treatment device, the tip assembly comprising:
   a) a hollow sleeve that defines a longitudinal axis and is adapted to releasably fit on the reusable surgical laser treatment device, wherein the sleeve includes a plurality of spaced apart longitudinally extending internal ribs adapted to be received in corresponding slits on the reusable laser surgical device,
   b) a cannula member that includes a first end having a diameter and a second end that tapers to a discharge tip end,
   c) an optical fiber axially positioned within the tip assembly and extending beyond the discharge tip end, and
   d) a connector for releasably connecting the sleeve to the reusable surgical laser treatment device, wherein the connector includes a housing having a diameter that is smaller than the first end of the cannula, such that the housing is received in the cannula, and a probe that is adapted to extend into the reusable surgical laser treatment device, and wherein the housing and the probe cooperate to define a longitudinal opening through which the optical fiber extends.

9. The disposable tip assembly of claim 8 wherein the discharge tip end is at a right angle to the sleeve longitudinal axis.

10. The disposable tip assembly of claim 8 wherein the connector comprises a magnetic material.

11. The disposable tip assembly of claim 8 wherein the housing comprises a magnetic material.

12. The disposable tip assembly of claim 8 wherein the housing has a larger diameter than the probe.

* * * * *